United States Patent [19]

Petchul et al.

[11] Patent Number: 5,376,366
[45] Date of Patent: Dec. 27, 1994

[54] COMPOSITION AND PROCESS FOR FORMING ISOPROPYL ALCOHOL GEL WITH WATER-SOLUBLE VINYL POLYMER NEUTRALIZING AGENT

[75] Inventors: John Petchul, 2221 Windy Hill La., Lake Orion, Mich. 48363; Rosemary Gaudreault, Park Ridge, Ill.

[73] Assignee: John Petchul, Lake Orion, Mich.

[21] Appl. No.: 974,535

[22] Filed: Nov. 12, 1992

[51] Int. Cl.$^5$ .................. A61K 7/48; A61K 7/32; A61K 7/06
[52] U.S. Cl. .................. 424/78.07; 424/78.03; 525/329.9
[58] Field of Search ............ 424/78.06, 78.02, 78.07; 514/772.3; 325/382; 525/327.9

[56] References Cited

U.S. PATENT DOCUMENTS

| | | | |
|---|---|---|---|
| 4,393,076 | 7/1983 | Noda et al. | 424/317 |
| 4,762,718 | 8/1988 | Marks, Sr. | 424/409 |
| 4,837,019 | 6/1989 | Georgalas et al. | 424/101 |
| 4,895,857 | 1/1990 | Blackman | 514/362 |
| 4,895,859 | 1/1990 | Blackman | 514/362 |
| 4,897,404 | 1/1990 | Blackman | 514/362 |
| 4,913,897 | 4/1990 | Chvapil et al. | 424/59 |
| 4,956,170 | 9/1990 | Lee | 514/772.1 |
| 5,034,221 | 7/1991 | Rosen et al. | 424/73 |
| 5,158,761 | 10/1992 | Kamishita et al. | 514/772.1 |
| 5,167,950 | 12/1992 | Lins | 424/47 |

*Primary Examiner*—Thurman K. Page
*Assistant Examiner*—Peter F. Kulkosky
*Attorney, Agent, or Firm*—Gifford, Groh, Sprinkle, Patmore and Anderson

[57] ABSTRACT

An isopropyl alcohol gel having use as a rubbing composition and having antiseptic properties. The isopropyl alcohol gel of the present invention comprises a polymer, water, isopropyl alcohol and a polymer neutralizing agent. The polymer is dispersed in water to create a thick phase. The preferred polymer is a carbomer resin that forms a slightly gelatinous mass through hydration of the polymer. The selected amount of isopropyl alcohol is added by dispersion to the polymer-water phase. The mixture is allowed enough time to fully hydrate. A neutralizing agent is thereafter added to neutralize the activity of the polymer. The neutralizing agent is preferably tetrahydroxypropyl ethylenediamine. The resulting product is in homogenous heavy clear gel form.

10 Claims, No Drawings

COMPOSITION AND PROCESS FOR FORMING ISOPROPYL ALCOHOL GEL WITH WATER-SOLUBLE VINYL POLYMER NEUTRALIZING AGENT

BACKGROUND OF THE INVENTION

I. Field of the Invention

The present invention relates to a process and composition for an isopropyl alcohol gel. More particularly, the present invention comprises the mixture of a polymer-water phase, isopropyl alcohol and a polymer neutralizing agent. The resulting product is a homogenous, heavy and clear gel that has use externally as an antiseptic and as a type of "rubbing alcohol".

II. Description of the Relevant Art

Propyl alcohols have long had use as chemical intermediates, solvents and antiseptics. Of the two propyl alcohols, n-propyl ($CH_3CH_2CH_2OH$) and isopropyl ($CH_3CHOHCH_3$), isopropyl alcohol has greater application. Derived from propylene by treatment with sulfuric acid followed by hydrolysis, isopropyl alcohol has particular utility as both an antiseptic and as a cooling and soothing liquid for external application.

In this latter application isopropyl alcohol has replaced ethyl alcohol as "rubbing alcohol". Rubbing alcohol typically contains approximately seventy percent denatured isopropyl alcohol.

Because of its relatively low value of heat of vaporization (288 Btu/lb.), isopropyl alcohol evaporates quickly at room temperature. It is this characteristic that gives the user the "cooling" sensation realized during application.

However, it is this same "cooling" characteristic that reflects the fleeting nature of liquid isopropyl alcohol thinly spread at room temperature—the cool sensation is caused by the rapid evaporation of the liquid.

As noted, one of the valuable uses of isopropyl alcohol is as an antiseptic medication. This quality makes the liquid particularly useful for home use as well as for more complex, clinical medical procedures. However, because of the above-described tendency of isopropyl alcohol to quickly evaporate, the liquid serves only limited function as an antiseptic. While temporarily sterilizing wounds and the areas around wounds, once the isopropyl alcohol evaporates, the wounded area is again open to infection and disease.

As may now be more clearly understood, many external applications of isopropyl alcohol would be well served if a way of slowing the evaporation process were known. Accordingly, known approaches to applying isopropyl alcohol have failed to overcome this considerable drawback when used as an antiseptic.

SUMMARY OF THE PRESENT INVENTION

The present invention relates to an alcohol gel having use as a rubbing composition and having long-lasting antiseptic properties. The gel of the present invention comprises a polymer, water, an alcohol, and a polymer neutralizing agent.

The preferred alcohol is isopropyl alcohol, this material being selected because of its above-discussed cooling and antiseptic qualities.

The preferred polymer is a carbomer resin that forms a slightly gelatinous mass through hydration of the polymer. The selected amount of alcohol is added to the polymer-water phase, and the polymer neutralizing agent is thereafter included to form the present composition. The neutralizing agent is preferably tetrahydroxypropyl ethylenediamine.

The resulting composition is a homogenous, heavy and clear gel. The formulation provides the alcohol gel with an "emollient seal" characteristic that prevents the alcohol from quickly evaporating. Thus the alcohol gel of the present invention does not dry out.

The principal advantage of the present invention lies in this resistance to drying. When used as an antiseptic, this feature provides long-term protection against bacteria and disease. When used as a rubbing composition, the alcohol gel of the present invention allows long periods of use without the inconvenience commonly associated with conventional isopropyl alcohol.

Other objects and details of the present invention will become apparent from the following detailed description.

DETAILED DESCRIPTION OF THE PREFERRED EMBODIMENT OF THE PRESENT INVENTION

The composition of the present invention includes as its basic components a polymer-water phase, an alcohol and a polymer neutralizing agent.

The polymer-water phase is a product of the commingling of a polymer dispersed in water. It is this phase that produces the gel characteristic of the present composition. The preferred polymer is therefore one that has superior suspending, thickening and gel-forming properties when hydrated with water. Accordingly, the preferred polymer is one from the group of water-soluble vinyl polymers. Such polymers include Carbomer 940 for which there are several trade names, including Carbopol 940, produced by B. F. Goodrich Company, Cleveland, Ohio. While many of the resins of this group might deliver satisfactory results, Carbomer 940 is the selected product for application in the present invention. These polymers are appreciably soluble in water.

To create the polymer-water phase, the polymer is dispersed in a volume of water, with the ratio of water to polymer being approximately 25:1. Because of its appreciable solubility in water, Carbomer 940 is regarded as a "difficult-to-wet" powder. Accordingly, care should be taken to hydrate completely the powder by use of an efficient wet mixer such as the Quadro ™ -Ytron ® "ZC" (trademark; Quadro Engineering, Inc., Waterloo, Ontario). This unit is preferred because it is designed to disperse difficult-to-wet powders (such as Carbomer 940) into a liquid stream.

The resulting polymer-water phase reflects a smooth, consistent lump-free slurry, the molecular structure of which is undamaged. The resulting polymer-water phase is very thick and is somewhat slippery.

After producing the polymer-water phase, a quantity of an alcohol is added by dispersion. The volume of alcohol should be added in an alcohol to polymer-water phase ratio of approximately 2:1. To assure complete dispersion, the alcohol should be added to the polymer-water phase by again using a dispersion unit such as the above-mentioned Quadro ™ -Ytron ® "ZC".

The preferred alcohol is isopropyl alcohol, although it is conceivable that denatured ethyl alcohol may be used alternatively or additionally. Isopropyl alcohol is preferred because of its established antiseptic qualities. It also has value as a cooling and soothing liquid for external application.

After the alcohol is fully dispersed in the polymer-water phase, the composition is allowed to set for a period of time to allow the polymer to fully hydrate. This takes approximately eight to nine hours.

The hydrating time being completed, a polymer neutralizing agent is mixed into the polymer-water phase and alcohol combination. The preferred agent is tetrahydroxypropyl ethylenediamine. This is a colorless, viscous liquid that is particularly suited for use as a neutralizing agent for carbomer resins in the manufacture of gels. This agent is available under the tradename of Neutrol ® TE and is produced by the BASF Corporation, Wyandotte, Mich. The resulting composition is mixed until a homogenous, heavy clear gel is formed.

Gels containing tetrahydroxypropyl ethlenediamine are very compatible with alcohol.

The resulting gel is useful as both an antiseptic and as a rubbing gel. The gel form provides an emollient seal that restricts the evaporation of the alcohol without compromising its effectiveness. The composition leaves the skin feeling pleasantly smooth.

The gel of the present invention is physiologically compatible with human epidermis, having a pH of above 8.00. The viscosity of the resulting gel is 100,000 cps. The gel may be broken down for cleanup with a detergent solution.

The general ranges of the percent by weight of the constituent parts of the present composition are as follows:

Isopropyl Alcohol = 45.0–99.0 percent by weight;
Water = 1.0–55.0 percent by weight;
Neutralizing Agent = 3.0–5.0 percent by weight;
Polymer = 0.5–2.5 percent by weight.

The invention will be better understood from a consideration of the following example. All percentages are based upon weight.

EXAMPLE

Process for Producing Isopropyl Alcohol Gel Composition

As discussed, the polymer-water phase contains a water-soluble vinyl polymer and water. According to the present example, the polymer-water phase was established by dispersing 1.30 percent by weight Carbomer 940 into 32.16 percent by weight water. Dispersion was accomplished by use of a Quadro ™-Ytron ® mixer. The resulting phase was very thick.

Thereafter, 62.64 percent by weight isopropyl alcohol was added to the polymer-water phase, again by dispersion of the alcohol into the phase by using a Quadro ™-Ytron ® mixer. Approximately eight hours was allowed to pass during which time the polymer was allowed to fully hydrate.

Following complete hydration, 3.90 percent by weight of the polymer neutralizing agent tetrahydroxypropyl ethylenediamine was added to the composition by mixing which continued until a homogenous, heavy and clear gel was formed.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A process for preparing a gelatinous composition of matter having a pH above 8.00 and a viscosity of approximately 100,000 cps for external application, said process including the steps of:

preparing a water-soluble vinyl polymer-water phase by dispersing a water-soluble vinyl polymer in water, said water-soluble vinyl polymer being between 0.5 and 2.5 percent by weight and said water being between 1.0 and 55.0 percent by weight, the ratio of water to polymer being approximately 25:1;

adding an alcohol by dispersion to the water-soluble vinyl polymer-water phase, said alcohol being 45.0–99.0 percent by weight, the ratio of alcohol to said water-soluble vinyl polymer-water phase being approximately 2:1;

allowing enough time so that said water-soluble vinyl polymer becomes hydrated;

adding an agent to neutralize said water-soluble vinyl polymer, said agent being between 3.0–5.0 percent by weight; and mixing the composition.

2. The process of claim 1 wherein said alcohol is isopropyl alcohol.

3. The process of claim 1 wherein said addition of said alcohol is by dispersion.

4. The process of claim 1 wherein the time for hydrating is between eight and nine hours.

5. The process of claim 1 wherein said neutralizing agent is tetrahydroxypropyl ethylenediamine.

6. The process of claim 1 wherein said mixing of said composition is affected until a homogenous heavy clear gel is formed.

7. The process of claim 1 wherein between 1.0 and 55.0 percent by weight of water is used.

8. The process of claim 7 wherein between 45.0 and 99.0 percent by weight of alcohol is used.

9. The process of claim 8 wherein between 0.5 and 2.5 percent by weight of polymer is used.

10. The process of claim 9 wherein between 3.0 and 5.0 percent by weight of neutralizing agent is used.

* * * * *

UNITED STATES PATENT AND TRADEMARK OFFICE
CERTIFICATE OF CORRECTION

PATENT NO. : 5,376,366
DATED : December 27, 1994
INVENTOR(S) : John Petchul
Rosemary Gaudreault It is certified that error appears in the above-indentified patent and that said Letters Patent is hereby corrected as shown below:

Column 4, line 14, "above" should be --about--.

Signed and Sealed this

Eighteenth Day of July, 1995

Attest:

BRUCE LEHMAN

Attesting Officer    Commissioner of Patents and Trademarks